United States Patent [19]

Hunter, Jr.

[11] 4,071,613
[45] Jan. 31, 1978

[54] STABILIZED ALCOHOL SOLUTION OF REDUCING SALT FORMULATIONS FOR USE IN PREPARING RADIOISOTOPE LABELED SCANNING AGENTS: LIVER SCANNING TECHNETIUM-99m COLLOID AND METHOD OF PREPARATION

[75] Inventor: William Ward Hunter, Jr., Fresno, Ohio

[73] Assignee: Abbott Laboratories, North Chicago, Ill.

[21] Appl. No.: 661,469

[22] Filed: Feb. 26, 1976

[51] Int. Cl.² .................. A61K 43/00; A61K 29/00
[52] U.S. Cl. .................. 424/1; 252/301.1 R; 252/309; 424/9
[58] Field of Search .................. 424/1, 115, 9, 198, 424/359; 252/301.1 R, 301.1 S, 309; 250/303

[56] References Cited
U.S. PATENT DOCUMENTS 3,875,299  4/1975  Winchell et al. .................. 424/1
3,962,412  6/1976  Wolfangel .................. 424/1

OTHER PUBLICATIONS

Lin, Journal of Nuclear Medicine, vol. 13, No. 1, Jan., 1972, pp. 58–65.

Primary Examiner—Benjamin R. Padgett
Assistant Examiner—Christine M. Nucker
Attorney, Agent, or Firm—Robert D. Weist; Robert L. Niblack

[57] ABSTRACT

A stabilized alcohol solution of reducing salt formulations has been developed and applied to the development of such agents as a radiolabeled liver scanning agent comprising colloids of technetium-99m and a reducing agent selected from the group of $SnCl_2$, $TiCl_3$, $CrCl_2$ and $FeCl_2$ and other salts, with or without a stabilizing agent, a bone scanning agent comprising a phosphate complex and a lung scanning agent comprising macro aggregated albumin.

7 Claims, No Drawings

STABILIZED ALCOHOL SOLUTION OF REDUCING SALT FORMULATIONS FOR USE IN PREPARING RADIOISOTOPE LABELED SCANNING AGENTS: LIVER SCANNING TECHNETIUM-99m COLLOID AND METHOD OF PREPARATION

FIELD OF THE INVENTION

This invention relates to a stabilized solution of reducing salt formulations for use in preparing labeled scanning agents, and more particularly to liver scanning agents employing colloids of technetium-99m and reducing agents such as $SnCl_2$, $TiCl_3$, $CrCl_2$ and $FeCl_2$ and other salts.

BACKGROUND OF THE INVENTION

Comparison studies have shown the value of reticuloendothelial system, RES (e.g. liver, spleen and bone marrow), scanning with radionuclides as a diagnostic tool. The use of a variety of radioisotope labeled particles or colloids for scanning procedures is well documented in the literature, and the behavior of particles as a function of liver blood flow dynamics has been described in detail.

As with all scanning preparations in general, the most desirable agent is that which combines good target organ localization and high efficiency labeling characteristics with a short lived radioisotope. Stability of the labeled agent and ease of preparation are also essential to meet the particular demands of clinical usage. Safety to the patient is the foremost criterion by which agents meeting the above practical requirements must be judged.

Certain metal ion compounds (e.g. tin, titanium, iron and chromium), whose biological distribution, toxicity and fate in animals have been studied, can be readily prepared as colloidal particles, a size range not filtered out by the lung and ideal for obtaining high target to background ratios in the liver.

Generally, a RES scanning agent is chemically a radioactive colloid when administered intravenously. The colloid particles are phagocytized by the reticuloendothelial cells, such as the Kupffer cells, of the liver. These particles accumulate rapidly in the Kupffer cells and other RES cells and remain there long enough for scintillation scans of their distribution to be obtained. The position, size, shape of the liver or any space occupying lesion in the liver of sufficient size can be readily localized and determined by radioisotope uptake in healthy tissue and lack of uptake at the site of the lesions.

The metastable isotope Tc-99m has a 6 hour half-life and lacks primary particulate radiation. These properties reduce radiation exposure to the patient. This improves the quality of the scan and decreases the total time required to complete the procedure.

Because of the six-hour physical half-life of Tc-99m, the routine use of the Tc-99m labeled liver scanning agent requires daily compounding. Therefore, it is desirable to have a stable non-radioactive preparation for a liver agent containing all the components required to prepare the agent as needed.

Although Tc-99m compounds would appear to be ideal radio-pharmaceuticals for diagnostic use, providing or selecting technetium compounds or colloids with a view toward organ specificity and tolerable levels of toxicity is a complex task. Obviously, compounds with a very low $LD_{50}$ are undesirable for human or veterinary use, even in the small amounts called for by diagnostic work. Compounds with insufficient in vivo stability may be poor diagnostic tools, since the radioactive ions or other chemical species with insufficient or undesirable organ specificity may be liberated. Stable compounds which become distributed generally throughout the organism, despite their stability, or which do not reach a desired destination in the organism are also poorly suited for many studies of organ function or structure, e.g. liver and gall bladder studies.

The problem of selecting or preparing a liver specific radio-pharmaceutical for liver morphology studies is particularly difficult. Any radio-pharmaceutical used for this purpose should ideally have 100% RES specificity and minimal uptake in other organs. One such agent is disclosed in U.S. Pat. No. 3,875,299. However, the tin colloid of that patent suffers the disadvantage of requiring water as the solvent which tends to cause hydrolysis and premature formation of the colloid and is highly sensitive to air oxidation.

A BRIEF SUMMARY OF THE INVENTION

Briefly, this invention consists of a stabilized solution of reducing salt formulations for use in preparing radioisotope-labeled scanning agents such as a metal hydroxide colloid formed from stannous chloride and technetium in aqueous solution; however, other agents as $TiCl_3$, $CrCl_2$ and $FeCl_2$ and other salts may be used with the technetium. The resulting Tc-99m complex is suitable for injection into the bloodstream of a mammal in a biologically sterile aqueous medium substantially isotonic with mammalian body fluids. A meaningful picture of the reticuloendothelial system of the liver and RES morphology will be obtained by measuring the radioactivity emitted from the liver and RES, with normally minimal uptake by the lungs of the patient being studied.

The liver scanning agent preferably consists of a colloid formed from stannous chloride which is highly superior to marketed sulfur colloids in ease of preparation; however, colloids of $TiCl_3$, $CrCl_2$ or $FeCl_2$ and other salts may be used. Only one or two simple steps are required to prepare the liver agent for injection, that is, the addition of technetium to the vial of the liver agent at room temperature, which may or may not be followed by a second addition of either mannitol, cyclic alcohol or sodium bicarbonate as a stabilizer.

It has been found that suitable Tc-99m metal ion hydroxide colloids can be formed in the presence of other anhydrous solvents such as ethers, an aliphatic alcohol or ethanol. The particles formed have high liver retention characteristics, are stable for an extended time period, either with or without stabilizer, and are notable in their ease of preparation. The use of an anhydrous solvent is preferred because such a water-free solvent stabilizes the reducing salt while minimizing hydrolysis and premature formation of the colloid. This is due to the protective effect exerted by the solvent on the metal ions in solution. Additionally, the anhydrous solvent decreases the reductant sensitivity to air oxidation.

Aliphatic alcohols mean and include open chain carbon compounds having an alcohol group such as and including, but not limited to isobutyl alcohol, butyl alcohol, propyl alcohol, isopropyl alcohol, etc.

It has also been found that the use of an anhydrous solvent imparts several additional advantages to the inventive colloid. Of greatest importance to the handling is the fact that due to the decreased sensitivity to air oxidation, production is easier and the process handling is simplified. Also of importance is that with the use of such a solvent, the colloid is stable for extended time periods, and there is no increase in colloid size. Thus, lung uptake is maintained at a minimal level.

Colloids of Tc-99m stannous chloride were prepared following the steps hereinafter described.

EXAMPLE 1

$SnCl_2$ solution was prepared by dissolving 25 mg of $SnCl_2$, anhydrous, in 50 ml of absolute ethyl alcohol, ether or an aliphatic alcohol. This solution contained 50 μg of $SnCl_2$ in 0.1 ml. 0.1 ml of the $SnCl_2$ solution was pipetted into a vial to which 4 ml of 99Mo-99M-Tc generator eluate containing 4–50 mCi of Tc-99M was added. The $SnCl_2$-eluate solution was mixed well and then allowed to stand for 15 minutes. After standing for a specified time period, the solution was ready for use. However, if desired, the solution may be used immmediately after constitution since the colloid has been formed.

After thoroughly mixing, tagging efficiency, organ determination in mice, and pH were determined. The results in ten preparations, indicating good reproducibility of the formula, are given in the following table.

The prepared solution is intended for multi-dose human use with doses of 2–4 mCi each, and a recommended injection volume of 0.3 to 2.0 ml.

TABLE I

| Tagging Efficiency (% Bound 99$^m$Tc) | % Dose/Organ (2 mice) | | | |
|---|---|---|---|---|
| | Liver | Lung | Carcass | pH |
| 98.9 | 90.3 | 0.8 | 8.9 | 4.5 |
| 99.4 | 93.1 | 0.2 | 6.7 | 4.8 |
| 99.8 | 92.0 | 1.4 | 6.6 | 4.3 |
| 95.0 | 91.5 | 0.3 | 8.2 | 4.3 |
| 97.7 | 95.0 | 0.5 | 4.5 | 4.2 |
| 99.9 | 95.7 | 0.3 | 4.0 | 4.2 |
| 98.7 | 94.0 | 0.4 | 5.6 | 4.3 |
| 97.8 | 96.4 | 0.6 | 3.0 | 4.2 |
| 96.4 | 92.3 | 1.0 | 6.7 | 4.2 |
| 99.9 | 92.6 | 0.4 | 7.0 | 4.2 |
| Avg. 98.4±1.6 | 93.3±0.2 | 0.6±0.3 | 6.1±1.8 | 4.3±0.1 |

Examination of Table 1 illustrates that the pH of $SnCl_2$-eluate mixture was in the range of 4.5 ± 0.3; however, as noted in Table II the pH of the tagging solution can be in the range of 3–7. Therefore, it was not necessary to use a buffer solution to further adjust the pH.

TABLE II

| pH OF THE TAGGING SOLUTION | | | | |
|---|---|---|---|---|
| pH of Tagging Solution | pH of 99$^m$Tc-Sn Colloid | % Dose/Organ (2 Mice) | | |
| | | Liver | Lung | Carcass |
| 2.1 | 2.1 | 38.1 | 2.1 | 59.8 |
| 3.1 | 3.0 | 90.0 | 1.5 | 8.5 |
| 4.0 | 4.0 | 87.8 | 0.7 | 11.5 |
| 5.2 | 4.5 | 88.0 | 0.7 | 11.3 |
| 6.5 | 4.8 | 93.1 | 0.2 | 6.7 |
| 7.1 | 4.8 | 80.4 | 1.7 | 17.9 |
| 7.5 | 5.0 | 63.6 | 0.8 | 35.6 |

Even though the tests of Example 1 were performed using a 25 μg concentration of $SnCl_2$, Table III clearly illustrates that the product works effectively with a concentration of $SnCl_2$ in the range of 2–200 μg.

TABLE III

| $SnCl_2$ Concentratin (μg) | SnCl$_2$ CONCENTRATION | | | | |
|---|---|---|---|---|---|
| | Tagging Efficiency (% Bound 99$^m$Tc) | % Dose/Organ (2 Mice) | | | |
| | | Liver | Lung | Spleen | Carcass |
| 25 | 96.0 | 94.2 | 0.4 | 1.0 | 4.4 |
| 50 | 99.7 | 96.4 | 0.4 | 1.4 | 1.8 |
| 100 | 99.5 | 95.0 | 0.4 | 1.7 | 2.9 |
| 150 | 99.6 | 95.9 | 0.7 | 1.4 | 2.0 |
| 200 | 99.6 | 95.0 | 0.6 | 2.1 | 2.3 |

It can be noted from an observation of Tables IV and V that a change in either the volume of the generator eluate (between 1–8 ml) or a change in the volume of the solvent (between 0.1–2.5 ml) had an insignificant effect on the effectiveness of the liver agent.

TABLE IV

| Volume of Ethanol (ml) | VOLUME OF ETHANOL | | | |
|---|---|---|---|---|
| | Tagging Efficiency % Bound 99$^m$Tc | % Dose/Organ (2 Mice) | | |
| | | Liver | Lung | Carcass |
| 0.1 | 96.3 | 93.8 | 0.7 | 5.5 |
| 0.2 | 97.8 | 95.7 | 0.5 | 3.8 |
| 0.5 | 97.5 | 91.8 | 0.5 | 7.7 |
| 1.0 | 96.8 | 89.5 | 1.1 | 9.4 |
| 2.0 | 97.3 | 87.5 | 0.6 | 11.9 |
| 0.2 | 99.1 | 96.4 | 0.3 | 3.3 |
| 0.75 | 98.4 | 93.8 | 0.5 | 5.7 |
| 1.0 | 99.7 | 93.8 | 1.0 | 5.2 |
| 2.0 | 94.9 | 89.0 | 1.0 | 10.0 |
| 2.5 | 96.0 | 90.3 | 2.0 | 7.7 |

TABLE V

| Volume of Eluate (ml) | VOLUME OF ELUATES | | | |
|---|---|---|---|---|
| | Tagging Efficiency (% of Bound 99$^m$Tc) | % Dose/Organ (2 Mice) | | |
| | | Liver | Lung | Carcass |
| 1 | 99.5 | 96.4 | 0.2 | 3.4 |
| 2 | 98.9 | 95.4 | 0.5 | 5.1 |
| 4 | 99.6 | 95.8 | 0.3 | 3.9 |
| 6 | 96.2 | 96.2 | 0.1 | 3.7 |
| 8 | 95.8 | 95.8 | 0.4 | 3.8 |

EXAMPLE 2

To observe the effect of temperature, various solutions prepared in accord with Example 1, were incubated at different temperatures. The products appeared slightly cloudy after incubation at 65° and 100° C. It was also noted that with increase in temperature, no statistical difference in organ distribution occurred. However, as can be observed, temperature has very little effect over a range of temperature far exceeding that which would be encountered with many other preparations, such as 99$^m$Tc-sulfur colloid.

TABLE VI

| Temperature (° C) | Tagging Efficiency (% Bound 99$^m$Tc) | % Dose/Organ (2 Mice) | | | |
|---|---|---|---|---|---|
| | | Liver | Lung | Spleen | Carcass |
| 5 | 98.8 | 92.0 | 0.6 | 3.1 | 4.3 |
| 25 | 99.0 | 95.6 | 0.2 | 2.0 | 2.2 |
| 40 | 99.5 | 96.6 | 0.4 | 1.8 | 1.2 |
| 65 | 99.5 | 95.0 | 0.6 | 2.4 | 2.0 |
| 100 | 96.6 | 93.8 | 0.7 | 2.7 | 2.8 |

EXAMPLE 3

Several studies were run to determine the stability of the reconstituted liver agent.

The studies were carried out using 2–2.5 kg male New Zealand white rabbits. The rabbits were injected with 0.3 ml of labeled material into a marginal ear vein, and 15 minutes later blood samples were drawn and the animals sacrificed for organ studies.

The studies, summarized in Table VII, indicate that tagging appears to be complete within 3 minutes and remains high for at least 7 hours.

TABLE VII

| Time Post-Reconstitution | Tagging Efficiency | Number of Determinations | Liver | Lung | Spleen | G.I. | Blood | Carcass | Kidneys | Number of Rabbits |
|---|---|---|---|---|---|---|---|---|---|---|
| 3 min. | 99.8 | 4 | | | | | | | | |
| 5 min. | 99.0 | 5 | | | | | | | | |
| 10 min. | 98.9 | 5 | 85.0 | 0.8 | 1.4 | 0.2 | 0.7 | 11.3 | 0.3 | 1 |
| 15 min. | 99.4 | 8 | 86.5 | 0.9 | 2.5 | 0.2 | 0.5 | 9.5 | 0.1 | 4* |
| 20 min. | 97.8 | 5 | 85.0 | 1.7 | 3.0 | 0.6 | 2.7 | 7.8 | 0.6 | 5 |
| 60 min. | 99.2 | 1 | 85.9 | 1.6 | 1.7 | 0.5 | 0.7 | 9.5 | — | 2 |
| 90 min. | 98.9 | 2 | 84.7 | 0.6 | 2.1 | 0.3 | 0.4 | 11.5 | 0.4 | 2 |
| 110 min. | 98.8 | 1 | 77.5 | 1.8 | 5.4 | 0.5 | 4.8 | 9.5 | 0.4 | 1 |
| 180 min. | 98.8 | 2 | 87.8 | 1.0 | 1.6 | 0.4 | 0.2 | 8.5 | 0.6 | 2 |
| 210 min. | 98.8 | 1 | 89.2 | 1.0 | 1.2 | 0.2 | 0.3 | 6.1 | 0.4 | 1 |
| 240 min. | 98.8 | 3 | 84.2 | 1.7 | 2.5 | 0.4 | 0.5 | 10.5 | 0.4 | 3* |
| 360 min. | 99.0 | 5 | 82.6 | 4.3 | 2.3 | 0.6 | 0.7 | 8.9 | 0.7 | 5 |
| 420 min. | 99.8 | 2 | 85.6 | 4.9 | 2.4 | 0.3 | 0.1 | 6.9 | 0.4 | 2 |
| 1440 min. | 97.4 | 2 | 65.3 | 20.2 | 1.2 | 1.3 | 1.5 | 10.5 | 1.1 | 2 |

*Kidneys average of two rabbits only.

EXAMPLE 4 a. Tc-99m distribution in mouse tissue.

In this study, three different preparations of Tc-99m-SnCl$_2$ colloid were used. Twenty-four mice were injected with 0.1 ml of each preparation and four mice were sacrificed 15 min., 2 hours, 4 hours, 6 hours, 12 hours and 24 hours after injection. The organs were removed and counted, and expressed as percentage of injected dose against standard.

TABLE VIII $^{99m}$Tc DISTRIBUTION (% OF INJECTED DOSE) IN TISSUES OF MICE AFTER INTRAVENOUS INJECTION OF $^{99m}$Tc-Sn COLLOID

| TIME AFTER INJECTION | LIVER | LUNG | HEART | SPLEEN | KIDNEYS | G.I. | CARCASS |
|---|---|---|---|---|---|---|---|
| 15 MIN. | 92.6±1.8 | 0.5±0.2 | <0.1 | 2.0±0.4 | 0.1±0.1 | 0.4±0.2 | 2.5±1.4 |
| 2 HRS. | 94.0±2.7 | 0.4±0.2 | <0.1 | 2.4±1.1 | 0.1±0.1 | 0.3±0.1 | 2.8±0.9 |
| 4 HRS. | 93.2±2.6 | 0.3±0.1 | <0.1 | 3.3±4.2 | 0.1±0.1 | 0.3±0.1 | 3.0±0.9 |
| 6 HRS. | 92.8±2.4 | 0.5±0.6 | <0.1 | 2.1±0.8 | 0.1±0.1 | 0.4±0.2 | 2.9±0.9 |
| 12 HRS. | 87.9±6.0 | 0.2±0.2 | <0.1 | 1.6±0.3 | 0.2±0.1 | 0.4±0.2 | 1.7±0.6 |
| 24 HRS. | 80.4±5.7 | 1.0±0.2 | 1.3±0.6 | 2.8±0.7 | 1.6±1.4 | 1.8±0.3 | 3.1±0.6 | b. Acute intravenous toxicity study in mice.

For this study, a solution containing 50 μg of SnCl$_2$, 0.2 ml ethanol and 2 ml of Tc-99m pertechnetate were used. A dose of a 20 gm. mouse equivalent to 0.5 ml for a 70 kg human was estimated at 0.000142 ml. The preparation was diluted to give the human multiple as indicated in Table IX. No adverse effect or death was observed over a 7 day observation period.

TABLE IX

ACUTE INTRAVENOUS MOUSE TOXICITY AND SYMPTOMATOLOGY

| GROUP | HUMAN MULTIPLE | DOSE (ml/kg)* | MORTALITY RATIO | OBSERVATIONS |
|---|---|---|---|---|
| 1 | 50 | 0.36 | 0/10 | No Toxic Effects Observed |
| 2 | 100 | 0.71 | 0/10 | " |
| 3 | 200 | 1.43 | 0/10 | " |
| 4 | 500 | 3.57 | 0/10 | " |
| 5 | 1250 | 8.93 | 0/10 | " |
| 6 | 2500 | 17.89 | 0/10 | " |

*Expressed as volume/weight equivalent of original undiluted preparations.

EXAMPLE 5

Ether and isobutyl alcohol tests (Table X below) clearly show these solvents to perform as well as ethanol. Tests were carried out to determine tagging efficiencies and organ distribution in mice.

TABLE X

USE OF DIFFERENT SOLVENTS

| Solvent | Tagging Efficiencies | Mouse Organ Distribution Data (Avg. 2 animals each) | | | | |
|---|---|---|---|---|---|---|
| | | Lung | Liver | Spleen | G.I. | Carcass |
| Diethyl ether | 99.8% 99.7% | 0.6% | 93.9% | 2.3% | 0.5% | 2.6% |
| Isobutyl alcohol | 99.6% 99.8% | 0.3% | 95.2% | 2.4% | 0.6% | 1.5% |

What I claim is:

1. An anhydrous stabilized organic solution for preparing a technetium-99m scanning agent, said solution comprising: a metal ion salt reductant for technetium and an anhydrous nonoxidizing organic solvent.

2. A solution as defined in claim 1 wherein said metal ion salt reductant is selected from the group consisting of SnCl$_2$, TiCl$_3$, CrCl$_2$ and FeCl$_2$.

3. A solution as defined in claim 2 wherein said metal ion salt reductant is SnCl$_2$.

4. A solution as defined in claim 1 wherein said solvent is selected from the group consisting of ethanol, ether and aliphatic alcohols.

5. A solution as set forth in claim 4 wherein said solvent is ethanol

6. An anhydrous stabilized organic solution consisting essentially of about 2 – 200 μg. of SnCl$_2$ and 0.1 – 2.5 ml. of ethanol.

7. A radiolabeled scanning agent comprising a colloid of technetium-99m and the solution of claim 1.

* * * * *